United States Patent [19]
Tjoeng et al.

[11] Patent Number: 5,985,862
[45] Date of Patent: *Nov. 16, 1999

[54] PHARMACEUTICAL COMPOSITIONS HAVING STEROID NITRATE ESTER DERIVATIVES USEFUL AS ANTI-INFLAMMATORY DRUGS

[75] Inventors: Foe S. Tjoeng, Manchester; Mark G. Currie, St. Charles, both of Mo.; Mark E. Zupec, O'Fallon, Ill.

[73] Assignee: G.D. Searle & Co., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/642,128

[22] Filed: May 2, 1996

[51] Int. Cl.$^6$ ..................................... A01N 45/00
[52] U.S. Cl. ........................... 514/171; 514/174; 552/276
[58] Field of Search ..................... 514/171, 174; 552/276

[56] References Cited

U.S. PATENT DOCUMENTS

| | | | |
|---|---|---|---|
| 3,639,434 | 2/1972 | Oxley et al. | 260/397.45 |
| 3,839,369 | 10/1974 | Hofmeister et al. | 260/397.45 |

FOREIGN PATENT DOCUMENTS

| | | |
|---|---|---|
| 1643034 | 5/1971 | Germany . |
| 2222491 | 11/1972 | Germany . |
| 2222491 | 11/1992 | Germany . |
| 4223800A1 | 1/1994 | Germany . |
| 1082573 | 9/1967 | United Kingdom . |
| 1082574 | 9/1967 | United Kingdom . |
| WO9403421-A2 | 2/1994 | WIPO . |
| WO9412463 | 6/1994 | WIPO . |
| WO9509831 | 4/1995 | WIPO . |

OTHER PUBLICATIONS

Translation of DE 2,222,491, Nov. 16, 1972.
Moncada et al, *Biochem.Pharm.* 38:1709–1715 (1989).
Moncada et al., *Pharm.Review* 43:109–147 (1991).
Moncada et al., *Jour.Cardio.Pharm.* 17:(1991), 525–527.
Persson et al., *Eur.Jour.Pharm.* 249 R7–R8 (1993).
Alspaugh & Granger, *Infection and Immunity*, 59:2291–2296 (1991).
Wallace et al., *Eur.Jour.Pharm.* 257:249–255 (1994).
MacIntyre et al., *Proc.Nat.Acad.Sci.* USA 88 2936–2940 (1991).
Pipili–Synetos et al, *Britis Journal of Pharmacology 116*, 1829–1834 (1995).

*Primary Examiner*—Dwayne C. Jones
*Attorney, Agent, or Firm*—Alan L. Scrivner; Dennis A. Bennett

[57] ABSTRACT

The present invention discloses novel pharmaceutical compositions having steroid nitrate ester($ONO_2$) derivatives, and to their use treating undesired smooth muscle contractions and inflammatory diseases.

12 Claims, No Drawings

PHARMACEUTICAL COMPOSITIONS HAVING STEROID NITRATE ESTER DERIVATIVES USEFUL AS ANTI-INFLAMMATORY DRUGS

BACKGROUND OF THE INVENTION

1. Field of the Invention

The present invention relates to novel pharmaceutical compositions containing steroid nitrate ester derivatives, and to their use treating inflammatory diseases.

2. Related Art

Steroids, specifically of the glucocorticoid class of molecules, are known to possess anti-inflammatory and immunomodulatory activities and are commonly utilized for the treatment of numerous autoimmune and inflammatory diseases. However, their beneficial effects are often slow to develop and accompanied by many dose-limiting side-effects. Nitric oxide donors, such as nitroglycerin, have also been utilized as pharmaceutical agents with prominent beneficial effects on the cardiovascular system. Many of the biological actions of nitric oxide potentially counteract the side-effects of the glucocorticoids and may enhance their therapeutic actions. The present invention relates to novel steroid nitrate ester derivatives that possess the combined biological properties of glucocorticoids and nitric oxide donors in a single molecule. These molecules have an advantage over currently utilized glucocorticoids in that they rapidly elicit beneficial pharmacological effects, such as bronchial relaxation, through the release of nitric oxide. It is intended that these novel molecules be utilized for therapy, in particular their use as anti-inflammatory and immunosuppressive drugs for the treatment of rheumatic diseases, immunological disorders, skin disorders, inflammation, transplant rejection, cancer, osteoporosis, rhinitis and asthma with less side-effects.

Glucocorticoids are commonly utilized for the pharmacologic treatment of inflammation and undesirable immune system reactions. These steroids have the capacity to prevent or suppress the development of inflammation resulting from a number of different injurious agents including infectious, immunological, chemical, mechanical, and radiation. Glucocorticoids are also effective in the treatment of immune system disorders including autoimmune diseases such as rheumatoid arthritis and lupus, and transplant rejection. However, the therapeutic applications of these steroids are somewhat limited due to toxicity and side-effects. The major side effects of the glucocorticoids are hypertension, peptic ulcers, increased susceptibility to infections, osteoporosis, hyperglycemia, and vascular occlusion.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite ester, glyceryltrinitrate and other nitrovasodilators. The recent identification of EDRF as NO has coincided with the discovery of a biochemical pathway by which NO is synthesized from the amino acid L-arginine by the enzyme nitric oxide synthase. The NO released by the constitutive enzyme acts as a transduction mechanism underlying several physiological responses. The NO produced by the inducible enzyme is a cytotoxic molecule for tumor cells and invading microorganisms.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). Furthermore, NO has been shown to possess anti-thrombotic (see Moncada et al. *Journal of Cardiovascular Pharmacology* 17, S25 (1991), Byrne et al., *World Patent application* WO09403421-A2 and Schonafinger et al., *German Patent application* DE4223800-A1), bronchorelaxant (Persson et al. *European Journal of Pharmacology*, 249, R7–R8 (1993), anti inflammatory, microbialcidal (Alspaugh and Granaer, *Infection and Immunity* 59, 2291–2296 (1991) and gastroprotective (see Wallace et al. *European Journal of Pharmacology*, 257, 249–255 (1994) effects in animal models. In addition, nitric oxide has been suggested to be effective against the loss of bone in in vitro models of osteoporosis (MacIntyre et al. *Proc.Natl.Acad.Sci.USA* 88, 2936–2940 (1991) and in inhibiting angiogenesis, tumor growth and metastasis in in vivo animal models (Pipili-Synetos et al. *British Journal of Pharmacology*, 116, 1829–1834 (1995).

The properties noted above make nitric oxide an ideal agent to enhance the actions of corticosteroids in the treatment of various diseases mentioned earlier by both increasing their biological effects as well as by reducing their side effects.

SUMMARY OF THE INVENTION

The present invention concerns novel pharmaceutical compositions comprising steroid nitrate derivatives of the Formula 1.

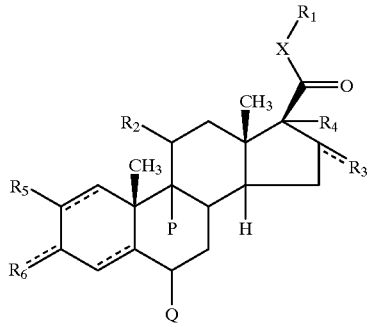

and pharmaceutically acceptable ester and prodrugs thereof, wherein;

the dotted lines in formula 1 indicate a single or a double bond;

$R_1$ is selected from the group consisting of hydrogen, hydroxy, nitrate ester ($ONO_2$), halogen, haloalkyl, nitroxyalkanoyl, thiol, heterocyclic, lower alkoxy, alkylsilyloxy, lower alkyl, wherein all said radicals may optionally be substituted with hydroxy, halogen, lower alkyl, lower alkenyl, lower alkynyl, lower alkoxy, amino, nitro, nitril, carboxyl and haloalkyl radicals or $R_1$ is a group of the formula OCO—$R_7$ wherein $R_7$ is alkanoic acid, lower alkyl, lower alkenyl, lower alkynyl, or lower alkoxy;

$R_2$ is nitrate ester ($ONO_2$);

$R_3$ and $R_4$ are independently selected from the group consisting of hydrogen, hydroxy, nitrate ester ($ONO_2$), nitroxyalkanoyl, lower alkyl, lower alkenyl, lower alkynyl and lower alkoxy, wherein all said radicals may optionally be substituted with hydroxy, lower alkyl, lower alkenyl, lower alkynyl, lower alkoxy, amino, nitro, nitril, carboxyl and haloalkyl radicals, or $R_3$ and $R_4$ are independently selected from a group of the formula OCO—$R_8$ wherein $R_8$ is 2-furanyl, lower alkyl or lower alkoxy group, or $R_3$ and $R_4$ may optionally form a cylic structure of the formula:

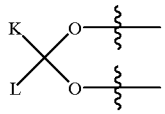

wherein, K and L are selected from the group consisting of hydrogen, and lower alkyl or optionally K and L can form a alicyclic ring or heterocyclic ring;

$R_5$ is hydrogen or halogen;

$R_6$ is hydrogen, hydroxy, or oxygen;

P and Q are independently selected from the group of hydrogen, chloro, fluoro and lower alkyl; and X is lower alkyl or sulfur if $R_1$ is haloalkyl.

The compositions defined above have usefulness as antiinflammatory and immunosuppressive drugs for treatment of rheumatic diseases, immunological disorders, skin disorders, inflammation, transplant rejection, osteoporosis, rhinitis and asthma. These compounds combine the previously described actions of the steroids and NO in a single molecule. The novel compositions of the present invention may exert their steroid activities directly with the NO still attached or after the NO is released.

DETAILED DESCRIPTION OF THE INVENTION

A preferred embodiment of the present invention is a compound of the formula (1)

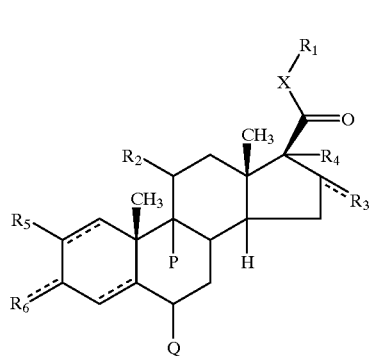

(1)

wherein;

the dotted lines in formula 1 indicate a single or a double bond;

$R_1$ is selected from the group consisting of hydrogen, hydroxy, nitrate ester (ONO$_2$), halogen, heterocyclic group of 2 to 5 carbon atoms and 1 to 2 hetero atoms, nitroxyalkanoyl group of 2 to about 6 carbon atoms, thio, haloalkyl group of 1 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, halogen, lower alkyl, lower alkenyl, lower alkynyl, lower alkoxy, amino, nitro, nitril, carboxyl and haloalkyl radicals, or $R_1$ is a group of the formula OCO—$R_7$ wherein $R_7$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms group;

$R_2$ is nitrate ester (ONO$_2$);

$R_3$ and $R_4$ are independently selected from the group consisting of hydrogen, hydroxy, nitrate ester (ONO$_2$), nitroxyalkanoyl group of 2 to about 6 carbon atoms, lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals or $R_3$ and $R_4$ are independently selected from a group of the formula OCO—$R_8$ wherein $R_8$ is 2-furanyl, lower alkyl group of 1 to about 6 carbon atoms or lower alkoxy group of 1 to about 6 carbon atoms;

$R_3$ and $R_4$ may optionally form a cylic structure of the formula;

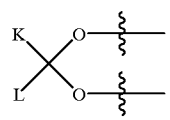

wherein, K and L are selected from the group consisting of hydrogen, lower alkyl group of 1 to about 8 carbon atoms, optionally K and L can form an alicyclic ring of 4 to about 8 carbon atoms or a heterocyclic ring of 4–6 carbon atoms and 1–2 heteroatoms selected from nitrogen, oxygen or sulfur;

$R_5$ is hydrogen or halogen;

$R_6$ is hydrogen, hydroxy or oxygen;

P and Q are independently selected from a group of hydrogen, chloro, fluoro and lower alkyl group of 1 to 6 carbon atoms; and X is lower alkyl group or sulfur if $R_1$ is a haloalkyl.

Another preferred embodiment of the present invention is a compound of the formula (1):

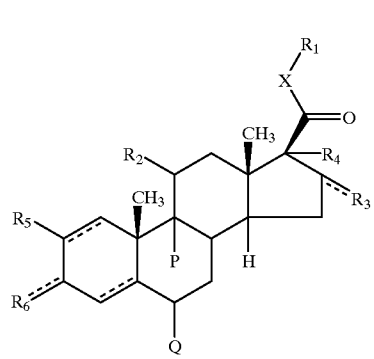

(1)

wherein;

the dotted lines in formula 1 indicate a single or a double bond;

$R_1$ is selected from the group consisting of hydrogen, hydroxy, nitrate ester (ONO$_2$), halogen, thiol, heterocyclic group of 3 to 4 carbon atoms and 1 to 2 hetero atoms, nitroxyalkanoyl group of 2 to about 4 carbon atoms, lower alkoxy group of 1 to about 4 carbon atoms, lower alkyl group of 1 to about 4 carbon atoms, wherein all said radicals may optionally be substituted with hydroxy, chloro, fluoro, lower alkyl, lower alkenyl, lower alkynyl, lower alkoxy, amino, nitro, nitril, carboxyl and haloalkyl radicals; or $R_1$ is a group of the formula OCO—$R_7$ wherein $R_7$ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms or lower alkoxy group of 1 to about 4 carbon atoms group;

$R_2$ is nitrate ester($ONO_2$);

$R_3$ and $R_4$ are independently selected from the group consisting of hydrogen, hydroxy, nitrate ester ($ONO_2$), nitroxyalkanoyl group of 2 to about 4 carbon atoms, lower alkyl group of 1 to about 4 carbon atoms, lower alkenyl group of 2 to about 4 carbon atoms, lower alkynyl group of 2 to about 4 carbon atoms, lower alkoxy group of 1 to about 4 carbon atoms, wherein all said radicals may optionally be substituted with hydroxy, lower alkyl, lower alkenyl, lower alkynyl, lower alkoxy, amino, nitro and haloalkyl radicals, or $R_3$ and $R_4$ is a group of the formula OCO—$R_8$ wherein $R_8$ is 2-furanyl, lower alkyl group of 1 to about 4 carbon atoms or lower alkoxy group of 1 to about 4 carbon atoms; or $R_3$ and $R_4$ may together optionally form a cylic structure of the formula:

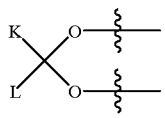

wherein, K and L are selected from the group consisting of hydrogen, and lower alkyl group of 1 to about 6 carbon atoms; optionally K and L can form a alicyclic ring of 5–8 carbon atoms or a heterocyclic ring of 4–5 carbon atoms and 1–2 heteroatoms selected from nitrogen, oxygen or sulfur;

$R_5$ is hydrogen or halogen;

$R_6$ is hydrogen, hydroxy, or oxygen;

P and Q are independently selected from the group consisting of hydrogen, chloro, fluoro and lower alkyl group of 1 to 4 carbon atoms; and X is methylene or sulfur if $R_1$ is a haloalkyl.

Another preferred embodiment of the present invention is a compound of the formula (1):

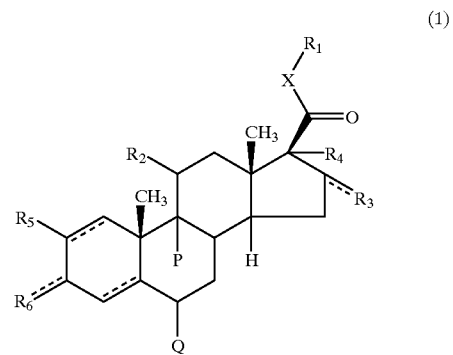

(1)

wherein;

the dotted lines in formula 1 indicate a single or a double bond;

$R_1$ is selected from the group consisting of hydrogen, hydroxy, nitrate ester ($ONO_2$), chloro, thiol, lower alkyl group of 1 to 4 carbon atoms; or $R_1$ is a group of the formula OCO—$R_7$ wherein $R_7$ is propanoic acid, methyl or ethyl;

$R_2$ is nitrate ester ($ONO_2$);

$R_3$ and $R_4$ are independently selected from the group consisting of hydrogen, hydroxy, nitrate ester ($ONO_2$), methyl, lower alkynyl group of 2 to 4 carbon atoms; or $R_3$ and $R_4$ are of formula OCO—$R_8$ wherein $R_8$ is ethoxy, 2-furanyl, methyl, ethyl, propyl or butyl; or $R_3$ and $R_4$ may together optionally form a cylic structure of the formula:

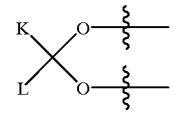

wherein, K and L are selected from the group consisting of hydrogen, methyl and butyl; or K and L can optionally form a cyclopentyl or cyclohexyl ring;

$R_5$ is hydrogen, chloro or bromo;

$R_6$ is hydroxy or oxygen;

P and Q are independently selected from a group of hydrogen, chloro, fluoro and methyl; and X is methylene.

While it may be possible for the preparations or compounds as defined above to be administered as the raw chemical, it is preferable to present them as a pharmaceutical formulation. Accordingly, the present invention provides a pharmaceutical formulation comprising a preparation or a compound as defined above or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a preparation or a compound as defined above or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for administration by inhalation can be prepared for use as an aerosolized medicaments such as in a manner recited in U.S. Pat. No. 5,458,135 and U.S. Pat. No. 5,447,150.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.01 to 500 mg/kg per day. The dose range for adult humans is generally from 0.1 mg to 1 g/day. Tablets or other forms of presentation provided in discrete units may conveniently contain an amount of compound of the invention which is effective at such dosage or as a multiple of the same, for instance, units containing 0.05 mg to 250 mg, usually around 0.1 mg to 100 mg.

The compounds of formula (I) are preferably administered by inhalation, orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethyl-butyn-1-yl radicals and the like.

The term "alicyclic hydrocarbon" means a aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkanoyl" means acyloxy radical with 2 to about 4 carbon atoms. Suitable examples include acetyloxy, propionyloxy and the like.

The term "halogen" means fluorine, chlorine, bromine or iodine.

The term "heterocyclic radical" means a saturated or unsaturated cyclic hydrocarbon radical with 4 to about 10 carbon atoms, preferably about 5 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkoxy" means the same as "alkoxy" except sulfur replaces oxygen.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

Starting materials used to make the present invention are commercially available such as from Sigma.

Many compounds of the present inventions have been made in the art. U.S. Pat. Nos. 3,930,970, 3,298,941 and 3,215,713, disclose a photochemical process for the preparation of diol mononitrates from alcohol nitrites. In U.S. Pat. Nos. 3,639,434, 3,743,741 and 3,839,369, the preparation of steroid nitrate esters and their uses as intermediates is disclosed. In German Patent 1643034, a method for the preparation of steroid nitrate esters is disclosed. In Canadian Patent 975755 and 969927, a process for the preparation and acidolysis of nitrate esters of 21-alcohols of the pregnene series is disclosed, respectively. In British Patent 1,082,573 and 1,082,574, a process for the preparation of steroid-11-nitrate esters and their uses as intermediates is disclosed. As noted above these references are hereby incorporated by reference as if written herein In addition to the processes disclosed in the art, the following scheme is useful for preparation of the compounds of the present invention.

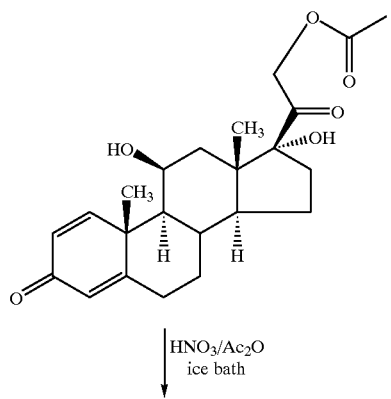

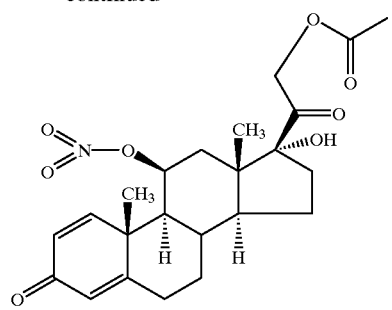

It will be obvious to one skilled in the art to make modifications in the choice of starting materials and process conditions to make all of the invention compounds disclosed herein.

The invention is further illustrated by the following examples.

EXAMPLE 1

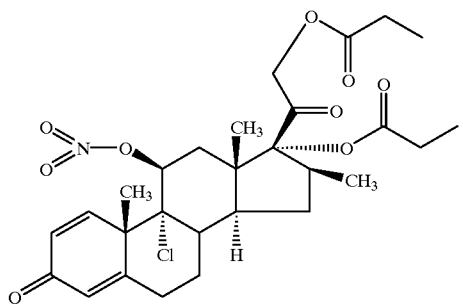

Fuming nitric acid (1 ml; d=1.49) and acetic anhydride (2.5 ml) were combined at −10° C. To this solution, a pre-cooled suspension of 9α-chloro-16β-methylprednisolone-17,21-dipropionate (0.5 g; 0.9 mmoles) in chloroform (20 ml) was added dropwise with stirring. The mixture was stirred for 4 h at 0° C. and poured into ice water (50 ml). The organic phase was separated and washed with water, saturated sodium bicarbonate solution and water. After drying over sodium sulfate overnight, the solid was filtered and the filtrate was taken down to dryness. The residue was purified on a Waters μBondapak column (30 cm×5 cm) using a linear gradient of 25–75% acetonitrile/water/trifluoroacetic acid. The desired fractions were collected and lyophilized to give 715 mg of white material. FAB-MS: $(M+Li)^+$=572.8; $^1$H-NMR (DMSO-$d_6$) δ 0.78 (s, 3H, $CH_3$(C-18)), 1.0–1.1 (m, 6H, $2CH_3$—$CH_2$), 1.2 (d, 3H, CH—$CH_3$), 1.53 (s, 3H, $CH_3$(C-19)), 2.35–2.45 (m, 4H, $2CH_3$—$CH_2$), 4.31 and 4.72 (2d, 2H, CO—$CH_2$—O), 5.6 (s, 1H, CH(C-11)), 6.05 (s, 1H, CH(C-4)), 6.28 (d, 1H, CH(C-2)), 7.1 (d, 1H, CH(C-1)).

EXAMPLE 2

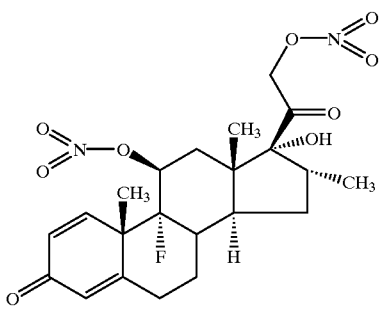

The title compound was prepared from 9α-fluoro-16α-methylprednisolone (0.5 g; 1.25 mmoles) in the same manner as described for EXAMPLE 1 except the amount of fuming nitric acid was doubled. FAB-MS: (M+Li)$^+$=489; $^1$H-NMR (CDCl$_3$) δ 0.91–0.99 (m, 6H, CH—CH$_3$ and CH$_3$(C-18)), 1.45 (s, 3H, CH$_3$(C-19)), 5.2(q, 2H, CO—CH$_2$—O), 5.56 (d, 1H, CH(C-11)), 6.2 (s, 1H, CH(C-4)), 6.38 (d, 1H, CH(C-2)), 6.78 (d, 1H, CH(C-1)).

EXAMPLE 3

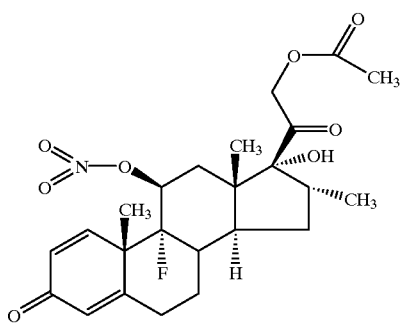

The title compound was prepared from 9α-fluoro-16α-methyl-prednisolone-21-acetate (1 g; 2.3 mmoles) in the same manner as described for EXAMPLE 1. FAB-MS: (M+Li)$^+$=486; $^1$H-NMR (CDCl$_3$) δ 0.93 (m, 6H, CH—CH$_3$ and CH$_3$(C-18)), 1.45 (s, 3H, CH$_3$(C-19)), 2.15 (s, 3H, CH$_3$CO), 4.7–5.0(q, 2H, CO—CH$_2$—O), 5.56 (d, 1H, CH(C-11)), 6.17 (s, 1H, CH(C-4)), 6.38 (d, 1H, CH(C-2)), 6.74 (d, 1H, CH(C-1)).

EXAMPLE 4

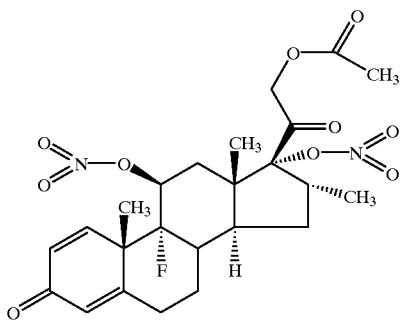

The title compound was prepared from 9α-fluoro-16α-methyl-prednisolone-21-acetate (1 g; 2.3 mmoles) in the same manner as described for EXAMPLE 1. FAB-MS: (M+Li)$^+$=531; $^1$H-NMR (CDCl$_3$) δ 1.03 (s, 3H, CH$_3$(C-18)), 1.07 (d, 3H, CH—CH$_3$), 1.45 (s, 3H, CH$_3$(C-19)), 2.22 (s, 3H, CH$_3$CO), 4.9(s, 2H, CO—CH$_2$—O), 5.58 (d, 1H, CH(C-11)), 6.17 (s, 1H, CH(C-4)), 6.42 (d, 1H, CH(C-2)), 6.78 (d, 1H, CH(C-1)).

EXAMPLE 5

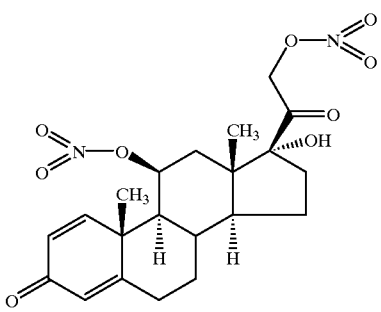

The title compound was prepared from prednisolone (1 g; 2.8 mmoles) in the same manner as described for EXAMPLE 1. FAB-MS: (M+Li)$^+$=457; $^1$H-NMR (DMSO-d$_6$) δ 0.67 (s, 3H, CH$_3$(C-18)), 1.29 (s, 3H, CH$_3$(C-19)), 5.61 (s, 1H, CH(C-11)), 5.3–5.6(q, 2H, CO—CH$_2$—O), 5.98 (s, 1H, CH(C-4)), 6.2 (d, 1H, CH(C-2)), 7.1 (d, 1H, CH(C-1)).

EXAMPLE 6

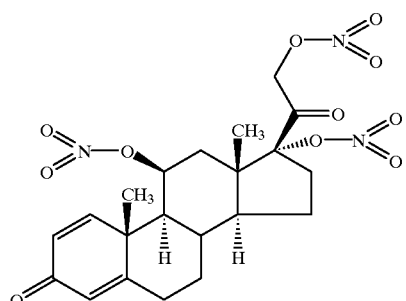

The title compound was prepared from prednisolone (1 g; 2.8 mmoles) in the same manner as described for EXAMPLE 1. FAB-MS: (M+H)$^+$=496.4; $^1$H-NMR (DMSO-d$_6$) δ 0.82 (s, 3H, CH$_3$(C-18)), 1.29 (s, 3H, CH$_3$(C-19)), 5.61 (d, 1H, CH(C-11)), 5.5–5.8(q, 2H, CO—CH$_2$—O), 5.98 (s, 1H, CH(C-4)), 6.18 (d, 1H, CH(C-2)), 7.03 (d, 1H, CH(C-1)).

EXAMPLE 7

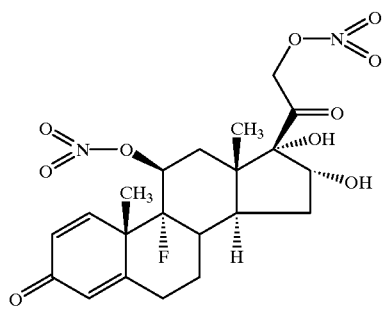

The title compound was prepared from 9α-fluoro-16α-hydroxyprednisolone (1 g; 2.5 mmoles) in the same manner as described for EXAMPLE 1. FAB-MS: (M+H)$^+$=485; $^1$H-NMR (DMSO-d$_6$) δ 0.99 (s, 3H, CH$_3$(C-18)), 1.48 (s, 3H, CH$_3$(C-19)), 5.3–5.45(q, 2H, CO—CH$_2$—O), 5.55 (d, 1H, CH(C-11)), 6.02 (s, 1H, CH(C-4)), 6.22 (d, 1H, CH(C-2)), 7.27 (d, 1H, CH(C-1)).

EXAMPLE 8

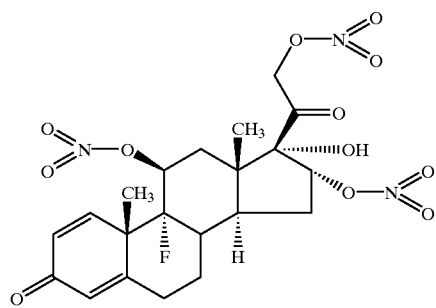

The title compound was prepared from 9α-fluoro-16α-hydroxy-prednisolone (1 g; 2.5 mmoles) in the same manner as described for EXAMPLE 1. FAB-MS: (M+H)$^+$=530; $^1$H-NMR (DMSO-d$_6$) δ 0.81 (s, 3H, CH$_3$(C-18)), 1.42 (s, 3H, CH$_3$(C-19)), 5.3–5.4(q, 2H, CO—CH$_2$—O), 5.49 (d, 1H, CH(C-11)), 6.08 (s, 1H, CH(C-4)), 6.28 (d, 1H, CH(C-2)), 7.03 (d, 1H, CH(C-1)).

EXAMPLE 9

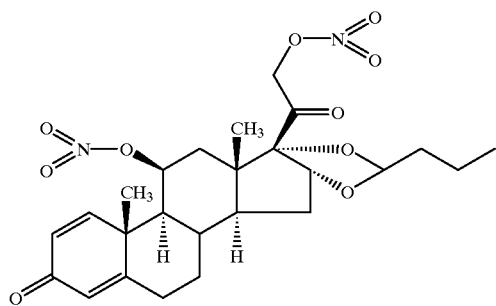

The title compound was prepared from 16α,17-butylidenedioxy-prednisolone (1 g; 2.3 mmoles) in the same manner as described for EXAMPLE 1. FAB-MS: (M+Li)$^+$= 527.7; $^1$H-NMR (CDCl$_3$) δ 0.92 (s,3H,CH$_3$(C-25)), 0.99 (s,3H,CH$_3$(C-18)), 1.36 (s,3H,CH$_3$(C-19)), 4.63 (t,1H,CH (C-21)), 4.87 (d,1H,CH(C-16)), 5.09 (t,1H,CH(C-21)), 5.16 (t,1H,CH(C-22)), 5.63–5.69 (m,1H,CH(C-11)), 6.09 (s,1H, CH(C-4)), 6.35 (d,1H,CH(C-2)), 6.88 (d,1H,CH(C-1)).

EXAMPLE 10

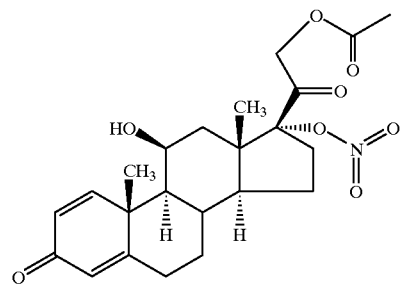

The title compound was prepared from prednisolone-21-acetate (1 g; 2.5 mmoles) in the same manner as described for EXAMPLE 1. FAB-MS: (M+H)$^+$=448; $^1$H-NMR (CDCl$_3$) δ 1.07(s,3H,CH$_3$(C-18)), 1.45 (s,3H,CH$_3$(C-19)), 2.20 (s, 3H,CH$_3$—CO), 4.50–4.55 (m,1H,CH(C-11)), 6.05 (s,1H,CH,(C-4)), 6.25 (d,1H,CH(C-2)), 7.25 (d,1H,CH(C-1)).

EXAMPLE 11

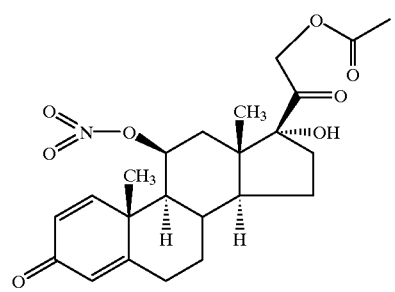

The title compound was prepared from prednisolone-21-acetate (1 g; 2.5 mmoles) in the same manner as described for EXAMPLE 1. FAB-MS: (M+H)$^+$=448; $^1$H-NMR (CDCl$_3$) δ 0.87 (s,3H,CH$_3$(C-18)), 1.36 (s,3H,CH$_3$(C-19)), 2.16 (s,3H,CH$_3$—CO), 5.63–5.67 (m,1H,CH(C-11)), 6.05 (s,1H,CH(C-4)), 6.30 (d,1H,CH(C-2)), 6.90 (d,1H,CH(C-1)).

EXAMPLE 12

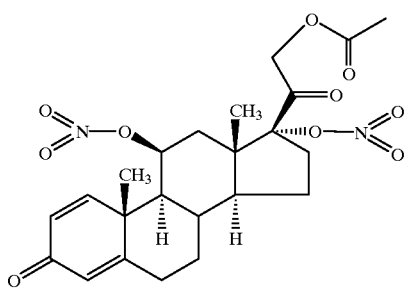

The title compound was prepared from prednisolone-21-acetate (1 g, 2.5 mmoles) in the same manner as described for EXAMPLE 1. FAB-MS: (M+H)$^+$=493; $^1$H-NMR (CDCl$_3$) δ 0.96 (s,3H,CH$_3$(C-18)), 1.35 (s,3H,CH$_3$(C-19)), 2.17 (s,3H,CH$_3$—CO), 4.60 (d,1H,CH(C-21)), 5.62–5.66 (m,1H,CH(C-11)), 6.08 (s,1H,CH(C-4)), 6.35 (d,1H,CH(C-2)), 6.90 (d,1H,CH(C-1)).

EXAMPLE 13

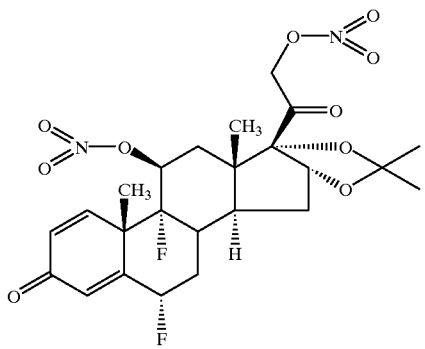

The title compound was prepared from 6α,9α-difluoro-16α-hydroxy-prednisolone-16,17-acetonide (1 g; 2.2 mmoles) in the same manner as described for EXAMPLE 1. FAB-MS: (M+Li)$^+$=549.4; $^1$H-NMR (CDCl$_3$) δ 0.84 (s,3H, CH$_3$(C-18)), 1.46 (s,3H,CH$_3$(C-19)), 5.00 (d,1H,CH(C-21)), 5.02 (d,1H,CH(C-16)), 5.34 (d,1H,CH(C-21)), 5.56–5.62 (m, 1H,CH(C-11)), 6.46 (d,1H,CH(C-2)), 6.5 (s,1H,CH(C-4)), 6.7 (d,1H,CH(C-1)).

EXAMPLE 14

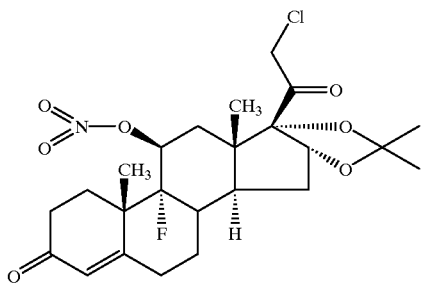

The title compound was prepared from 21-chloro-9α-fluoro-11β-hydroxy-16α,17α-isopropylidenedioxy-4-pregnene-3,20-dione (1 g; 2.2 mmoles) in the same manner as described for EXAMPLE 1. FAB-MS: (M+Li)$^+$=506.1; $^1$H-NMR (CDCl$_3$) δ 0.79 (d,3H,CH$_3$(C-18)), 1.46 (s,3H, CH$_3$(C-19)), 4.12 (d,1H,CH(C-21)), 4.58 (d,1H,CH(C-21)), 5.07 (d,1H,CH(C-16)), 5.50–5.56 (m,1H,CH(C-1l)), 5.84 (d,1H,CH(C-2)), 7.26 (s,1H,CH(C-1)).

EXAMPLE 15

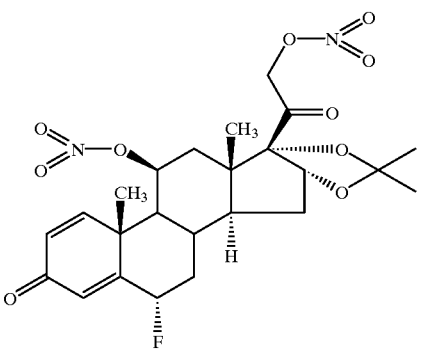

The title compound was prepared from 6α-fluoro-16α-hydroxy-prednisolone-16,17-acetonide (1 g; 2.3 mmoles) in the same manner as described for EXAMPLE 1. FAB-MS: (M+Li)$^+$=531.1; $^1$H-NMR (CDCl$_3$) δ 0.84 (s,3H,CH$_3$(C-18)), 1.47 (d,3H,CH$_3$(C-19)),4.98 (d,1H,CH(C-21)), 5.02 (d,1H,CH(C-16)), 5.34 (d,1H,CH(C-21)), 5.64–5.68 (m,1H, CH(C-11)), 6.42 (s,1H,CH(C-4)), 6.87 (d,1H,CH(C-2)), 7.25 (s,1H,CH(C-1)).

EXAMPLE 16

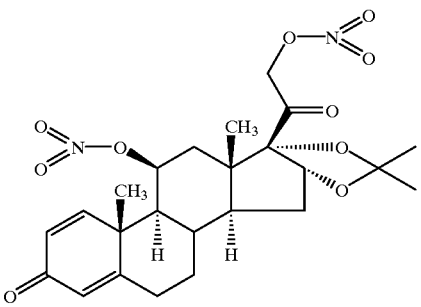

The title compound was prepared from 16α-hydroxyprednisolone-16,17-acetonide (1 g; 2.4 mmoles) in the same manner as described for EXAMPLE 1. FAB-MS: (M+Li)$^+$=513.1; $^1$H-NMR (CDCl$_3$) δ 0.84 (s,3H,CH$_3$(C-18)), 1.37 (s,3H,CH$_3$(C-19)), 4.99 (d,1H,CH(C-21)), 5.00 (d,1H CH(C-16)), 5.34 (d,1H,CH(C-21)), 5.64–5.68 (m,1H, CH(C-11)), 6.13 (s,1H,CH(C-4)), 6.38 (d,1H,CH(C-2)), 6.93 (d,1H,CH(C-1)).

EXAMPLE 17

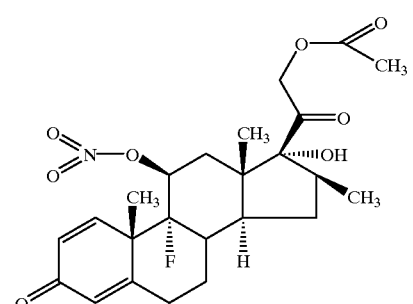

The title compound is prepared from 9α-fluoro-16β-methyl-prednisolone-21-acetate in the same manner as described for EXAMPLE 1.

EXAMPLE 18

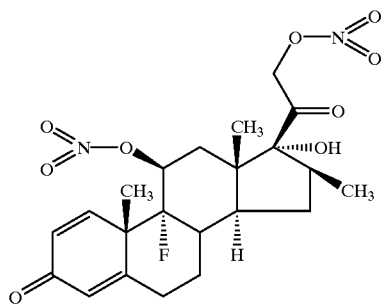

The title compound is prepared from 9α-fluoro-16β-methyl-prednisolone in the same manner as described for EXAMPLE 1.

EXAMPLE 19

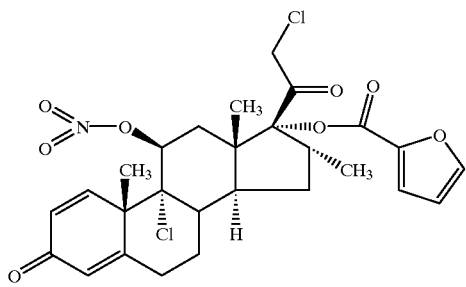

The title compound is prepared from 9α,21-dichloro-16α-methyl-prednisolone furoate in the same manner as described for EXAMPLE 1.

EXAMPLE 20

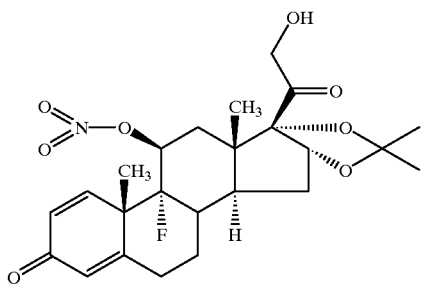

The title compound is prepared from 9α-fluoro-16α-hydroxy-prednisolone-16,17-acetonide in the same manner as described for EXAMPLE 1.

EXAMPLE 21

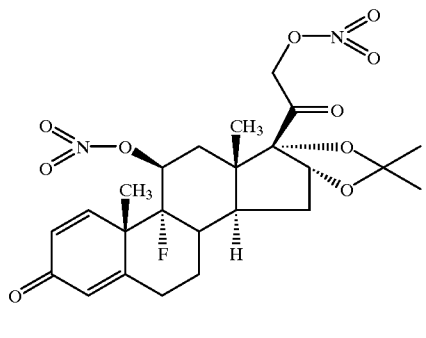

The title compound is prepared from 9α-fluoro-16α-hydroxy-prednisolone-16,17-acetonide in the same manner as described for EXAMPLE 1.

EXAMPLE 22

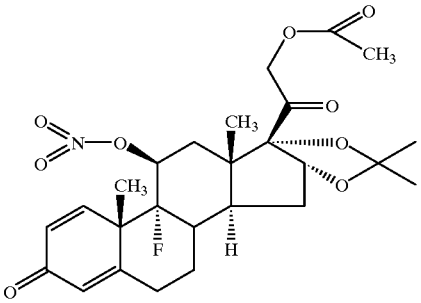

The title compound is prepared from 9α-fluoro-16α-hydroxy-prednisolone-16,17-acetonide-21-acetate in the same manner as described for EXAMPLE 1.

Biological Data

The subject compounds of the formula (1) have been found to be nitric oxide donors while maintaining their steroid activities and possess useful pharmacological properties as demonstrated in one or more of the following tests:

Selected compounds were tested in three in vitro and one in vivo assay. The in vitro assays consisted of the following: measuring the effect of the compounds to inhibit the increase of prostaglandins following treatment of human fetal fibroblast cells with interleukin-1 (IL-1) and interleukin-1 followed by arachidonic acid, measuring the effect of the compounds on cyclic GMP in the human fetal fibroblasts, and measuring the smooth muscle relaxant activity in rat aortic rings. The in vivo assay consists of measuring the antiinflammatory properties of the compounds in the carageenan treated rat air pouch model.

A. In vitro inhibition of prostaglandin $E_2$ ($PGE_2$) synthesis assay: Human fetal fibroblasts cells were treated with IL-1 for 16 hours and prostaglandin $E_2$ was measured by an ELISA. Compounds were given at the time of addition of IL-1. This assay provides an in vitro assessment of the compound to block the induction of the proinflammatory agent prostaglandin $E_2$ ($PGE_2$):

| Treatment | PGE$_2$ (ng) |
| --- | --- |
| Basal | 0.6 |
| IL-1 | 9.4 |
| IL-1 and Dexamethasone (10 uM) | 0.6 |
| IL-1 and Example 2 (10 uM) | 0.8 |
| IL-1 and Example 6 (10 uM) | 1.0 |

These data indicate that the steroids with the modifications for the generation of nitric oxide are effective at inhibiting the increase in PGE$_2$ and maintain the glucocorticoid action of the prevention of prostaglandin formation.

B. In vitro stimulation of CGMP production assay: Human fetal fibroblasts in the presence of isobutylmethylxanthine, an inhibitor of phosphodiesterase, were treated with compounds for 120 min and the intracellular cyclic GMP levels are measured by a radioimmunoassay. The cell line is utilized as a reporter cell assay to monitor the production of nitric oxide.

| Treatment well | fm cyclic GMP/cell |
| --- | --- |
| Basal | 145 |
| Example 1 | 170 |
| Example 2 | 260 |
| Example 3 | 350 |
| Example 4 | 225 |
| Example 5 | 485 |
| Example 6 | 330 |

These data show that the compounds possess the ability to increase cyclic GMP levels in the nitric oxide reporter cell assay, indicating that these compounds release nitric oxide during the treatment of the cells.

C. In vitro smooth relaxant activity assay: Selected compounds were examined for the ability to relax smooth muscle. The rat aortic ring assay was utilized as a bioassay to measure the relaxant activity. The rings were precontracted with phenylephrine (0.3 uM) and subsequently compounds were added to the tissue bath in the absence or in the presence of cysteine (Cys) and N$^G$-L-nitroarginine methyl ester (L-NAME):

I. In vitro smooth relaxant activity assay in the absence of Cys and L-NAME:

| Compound | Relaxation, EC$_{50}$ [$\mu$M] |
| --- | --- |
| beclomethasone dipropionate | >100 |
| Example 1 | >100 |
| dexamethasone | >100 |
| Example 2 | 1.5 |
| Example 4 | 10.0 |
| prednisolone | >100 |
| Example 5 | 5.0 |
| Example 6 | 10.0 |
| Budesonide | >100 |
| Example 9 | 3.0 |

II. In vitro smooth relaxant activity assay in the presence of Cys and L-NAME:

| Compound | Relaxation, EC$_{50}$ [$\mu$M] |
| --- | --- |
| beclomethasone dipropionate | >100 |
| Example 1 | 2.0 |
| budesonide | 100 |
| Example 9 | 10.0 |
| Example 11 | 40.0 |
| Example 14 | 70.0 |

Examples 1, 2, 4, 5, 6, and 9 were all tested in the absence of cysteine/NAME and, except for example 1, found to possess varying degrees of smooth muscle relaxant activity. In addition, examples 1, 9, 11, and 14 were also found to cause relaxation in the presence of cysteine and L-NAME. These data indicate that these compounds have smooth muscle relaxant activity, while the control compounds budesonide, dexamethasone, prednisolone and beclomethasone dipropionate did not show any effect.

D. In vivo anti inflammatory assay: Example 2 was tested for antiinflammatory activity in vivo in the rat carageenan air pouch assay. Rats are injected subcutaneously with a volume of air over several days to form pouch. Inflammation is subsequently induced in the pouch by the addition of the pro-inflammatory agent carageenan. The inflammation is measured by assaying the pouch fluid for prostaglandin E$_2$ by ELISA. Example 2 at 1 mg/kg dose blocked the increase in prostaglandin E$_2$ by 98%. These data indicate that these compounds possess the ability to reduce inflammation in vivo.

What is claimed is:

1. A method of treating a patient with inflammation by administering a therapeutically effective amount of the pharmaceutical composition having the formula:

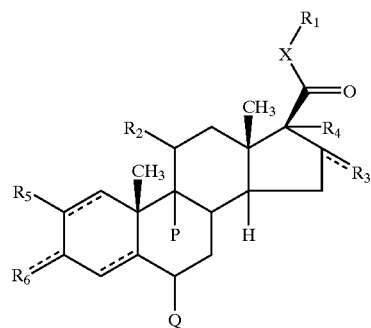

and pharmaceutically acceptable ester and prodrugs thereof, wherein;

the dotted lines in formula 1 indicate a single or a double bond;

R$_1$ is selected from the group consisting of hydrogen, hydroxy, nitrate ester (ONO$_2$), halogen, haloalkyl, nitroxyalkanoyl, thiol, heterocyclic, lower alkoxy, alkylsilyloxy, lower alkyl, wherein all said radicals may optionally be substituted with hydroxy, halogen, lower alkyl, lower alkenyl, lower alkynyl, lower alkoxy, amino, nitro, nitril, carboxyl and haloalkyl radicals or R$_1$ is a group of the formula OCO—R$_7$ wherein R$_7$ is alkanoic acid, lower alkyl, lower alkenyl, lower alkynyl, or lower alkoxy;

R$_2$ is nitrate ester (ONO$_2$);

R$_3$ and R$_4$ are independently selected from the group consisting of hydrogen, hydroxy, nitrate ester (ONO$_2$), nitroxyalkanoyl, lower alkyl, lower alkenyl, lower alkynyl and lower alkoxy, wherein all said radicals may optionally be substituted with hydroxy, lower alkyl, lower alkenyl, lower alkynyl, lower alkoxy, amino, nitro, nitril, carboxyl and haloalkyl radicals, or $R_3$ and $R_4$ are independently selected from a group of the formula OCO—$R_8$ wherein $R_8$ is 2-furanyl, lower alkyl or lower alkoxy group, or $R_3$ and $R_4$ may optionally form a cylic structure of the formula:

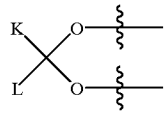

wherein, K and L are selected from the group consisting of hydrogen, and lower alkyl or optionally K and L can form a alicyclic ring or heterocyclic ring;

$R_5$ is hydrogen or halogen;

$R_6$ is hydrogen, hydroxy, or oxygen;

P and Q are independently selected from the group of hydrogen, chloro, fluoro and lower alkyl; and X is lower alkyl or sulfur if $R_1$ is haloalkyl; and together with a pharmaceutically acceptable carrier.

2. A method of treating a patient with inflammation by administering a therapeutically effective amount of the pharmaceutical compound recited in claim 1 wherein:

the dotted lines in formula 1 indicate a single or a double bond;

$R_1$ is selected from the group consisting of hydrogen, hydroxy, nitrate ester (ONO$_2$), halogen, heterocyclic group of 2 to 5 carbon atoms and 1 to 2 hetero atoms, nitroxyalkanoyl group of 2 to about 6 carbon atoms, thiol, haloalkyl group of 1 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, halogen, lower alkyl, lower alkenyl, lower alkynyl, lower alkoxy, amino, nitro, nitril, carboxyl and haloalkyl radicals, or $R_1$ is a group of the formula OCO—$R_7$ wherein $R_7$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms group;

$R_2$ is nitrate ester (ONO$_2$);

$R_3$ and $R_4$ are independently selected from the group consisting of hydrogen, hydroxy, nitrate ester (ONO$_2$), nitroxyalkanoyl group of 2 to about 6 carbon atoms, lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals or $R_3$ and $R_4$ are independently selected from a group of the formula OCO—$R_8$ wherein $R_8$ is 2-furanyl, lower alkyl group of 1 to about 6 carbon atoms or lower alkoxy group of 1 to about 6 carbon atoms;

$R_3$ and $R_4$ may optionally form a cylic structure of the formula;

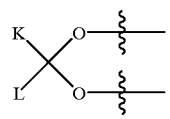

wherein, K and L are selected from the group consisting of hydrogen, lower alkyl group of 1 to about 8 carbon atoms, optionally K and L can form an alicyclic ring of 4 to about 8 carbon atoms or a heterocyclic ring of 4–6 carbon atoms and 1–2 heteroatoms selected from nitrogen, oxygen or sulfur;

$R_5$ is hydrogen or halogen;

$R_6$ is hydrogen, hydroxy or oxygen;

P and Q are independently selected from a group of hydrogen, chloro, fluoro and lower alkyl group of 1 to 6 carbon atoms; and X is lower alkyl group or sulfur if $R_1$ is a haloalkyl; and together with a pharmaceutically acceptable carrier.

3. A method of treating a patient with inflammation by administering a therapeutically effective amount of the pharmaceutical compound recited in claim 1 wherein:

the dotted lines in formula 1 indicate a single or a double bond;

$R_1$ is selected from the group consisting of hydrogen, hydroxy, nitrate ester (ONO$_2$), halogen, thiol, heterocyclic group of 3 to 4 carbon atoms and 1 to 2 hetero atoms, nitroxyalkanoyl group of 2 to about 4 carbon atoms, lower alkoxy group of 1 to about 4 carbon atoms, lower alkyl group of 1 to about 4 carbon atoms, wherein all said radicals may optionally be substituted with hydroxy, chloro, fluoro, lower alkyl, lower alkenyl, lower alkynyl, lower alkoxy, amino, nitro, nitril, carboxyl and haloalkyl radicals; or $R_1$ is a group of formula OCO—$R_7$ wherein $R_7$ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms or lower alkoxy group of 1 to about 4 carbon atoms group;

$R_2$ is nitrate ester(ONO$_2$);

$R_3$ and $R_4$ are independently selected from the group consisting of hydrogen, hydroxy, nitrate ester (ONO$_2$), nitroxyalkanoyl group of 2 to about 4 carbon atoms, lower alkyl group of 1 to about 4 carbon atoms, lower alkenyl group of 2 to about 4 carbon atoms, lower alkynyl group of 2 to about 4 carbon atoms, lower alkoxy group of 1 to about 4 carbon atoms, wherein all said radicals may optionally be substituted with hydroxy, lower alkyl, lower alkenyl, lower alkynyl, lower alkoxy, amino, nitro and haloalkyl radicals, or $R_3$ and $R_4$ is a group of the formula OCO—$R_8$ wherein $R_8$ is 2-furanyl, lower alkyl group of 1 to about 4 carbon atoms or lower alkoxy group of 1 to about 4 carbon atoms; or $R_3$ and $R_4$ may together optionally form a cylic structure of the formula:

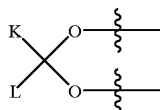

wherein, K and L are selected from the group consisting of hydrogen, and lower alkyl group of 1 to about 6 carbon atoms; optionally K and L can form a alicyclic ring of 5–8 carbon atoms or a heterocyclic ring of 4–5 carbon atoms and 1–2 heteroatoms selected from nitrogen, oxygen or sulfur;

$R_5$ is hydrogen or halogen;

$R_6$ is hydrogen, hydroxy, or oxygen;

P and Q are independently selected from the group consisting of hydrogen, chloro, fluoro and lower alkyl group of 1 to 4 carbon atoms; and X is methylene or sulfur if $R_1$ is a haloalkyl; and together with a pharmaceutically acceptable carrier.

4. A method of treating a patient with inflammation by administering a therapeutically effective amount of the pharmaceutical compound recited in claim 1 wherein:

the dotted lines in formula 1 indicate a single or a double bond;

$R_1$ is selected from the group consisting of hydrogen, hydroxy, nitrate ester ($ONO_2$), chloro, thiol, lower alkyl group of 1 to 4 carbon atoms; or $R_1$ is a group of the formula OCO—$R_7$ wherein $R_7$ is propanoic acid, methyl or ethyl;

$R_2$ is nitrate ester ($ONO_2$);

$R_3$ and $R_4$ are independently selected from the group consisting of hydrogen, hydroxy, nitrate ester ($ONO_2$), methyl, lower alkynyl group of 2 to 4 carbon atoms; or $R_3$ and $R_4$ are of formula OCO—$R_8$ wherein $R_8$ is ethoxy, 2-furanyl, methyl, ethyl, propyl or butyl; or $R_3$ and $R_4$ may together optionally form a cylic structure of the formula:

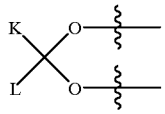

wherein, K and L are selected from the group consisting of hydrogen, methyl and butyl; or K and L can optionally form a cyclopentyl or cyclohexyl ring;

$R_5$ is hydrogen, chloro or bromo;

$R_6$ is hydroxy or oxygen;

P and Q are independently selected from a group of hydrogen, chloro, fluoro and methyl; and X is methylene; and together with a pharmaceutically acceptable carrier.

5. A method of treating a patient with undesired smooth muscle contractions by administering a therapeutically effective amount of the pharmaceutical composition having the formula:

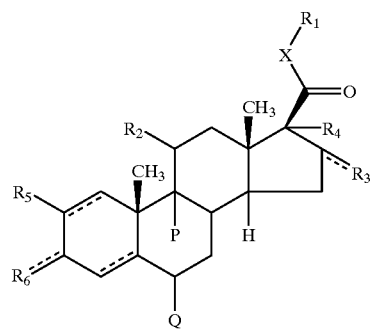

and pharmaceutically acceptable ester and prodrugs thereof, wherein;

the dotted lines in formula 1 indicate a single or a double bond;

$R_1$ is selected from the group consisting of hydrogen, hydroxy, nitrate ester ($ONO_2$), halogen, haloalkyl, nitroxyalkanoyl, thiol, heterocyclic, lower alkoxy, alkylsilyloxy, lower alkyl, wherein all said radicals may optionally be substituted with hydroxy, halogen, lower alkyl, lower alkenyl, lower alkynyl, lower alkoxy, amino, nitro, nitril, carboxyl and haloalkyl radicals or $R_1$ is a group of the formula OCO—$R_7$ wherein $R_7$ is alkanoic acid, lower alkyl, lower alkenyl, lower alkynyl, or lower alkoxy;

$R_2$ is nitrate ester ($ONO_2$);

$R_3$ and $R_4$ are independently selected from the group consisting of hydrogen, hydroxy, nitrate ester ($ONO_2$), nitroxyalkanoyl, lower alkyl, lower alkenyl, lower alkynyl and lower alkoxy, wherein all said radicals may optionally be substituted with hydroxy, lower alkyl, lower alkenyl, lower alkynyl, lower alkoxy, amino, nitro, nitril, carboxyl and haloalkyl radicals, or $R_3$ and $R_4$ are independently selected from a group of the formula OCO—$R_8$ wherein $R_8$ is 2-furanyl, lower alkyl or lower alkoxy group, or $R_3$ and $R_4$ may optionally form a cylic structure of the formula:

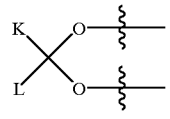

wherein, K and L are selected from the group consisting of hydrogen, and lower alkyl or optionally K and L can form a alicyclic ring or heterocyclic ring;

$R_5$ is hydrogen or halogen;

$R_6$ is hydrogen, hydroxy, or oxygen;

P and Q are independently selected from the group of hydrogen, chloro, fluoro and lower alkyl; and X is lower alkyl or sulfur if $R_1$ is haloalkyl; and together with a pharmaceutically acceptable carrier.

6. A method of treating a patient with undesired smooth muscle contractions by administering a therapeutically effective amount of the pharmaceutical compound recited in claim 5 wherein:

the dotted lines in formula 1 indicate a single or a double bond;

R₁ is selected from the group consisting of hydrogen, hydroxy, nitrate ester (ONO₂), halogen, heterocyclic group of 2 to 5 carbon atoms and 1 to 2 hetero atoms, nitroxyalkanoyl group of 2 to about 6 carbon atoms, thiol, haloalkyl group of 1 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, halogen, lower alkyl, lower alkenyl, lower alkynyl, lower alkoxy, amino, nitro, nitril, carboxyl and haloalkyl radicals, or R₁ is a group of the formula OCO—R₇ wherein R₇ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms group;

R₂ is nitrate ester (ONO₂);

R₃ and R₄ are independently selected from the group consisting of hydrogen, hydroxy, nitrate ester (ONO₂), nitroxyalkanoyl group of 2 to about 6 carbon atoms, lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals or R₃ and R₄ are independently selected from a group of the formula OCO—R₈ wherein R₈ is 2-furanyl, lower alkyl group of 1 to about 6 carbon atoms or lower alkoxy group of 1 to about 6 carbon atoms;

R₃ and R₄ may optionally form a cylic structure of the formula;

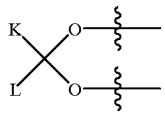

wherein, K and L are selected from the group consisting of hydrogen, lower alkyl group of 1 to about 8 carbon atoms, optionally K and L can form an alicyclic ring of 4 to about 8 carbon atoms or a heterocyclic ring of 4–6 carbon atoms and 1–2 heteroatoms selected from nitrogen, oxygen or sulfur;

R₅ is hydrogen or halogen;

R₆ is hydrogen, hydroxy or oxygen;

P and Q are independently selected from a group of hydrogen, chloro, fluoro and lower alkyl group of 1 to 6 carbon atoms; and X is lower alkyl group or sulfur if R₁ is a haloalkyl; and together with a pharmaceutically acceptable carrier.

7. A method of treating a patient with smooth muscle contractions by administering a therapeutically effective amount of the pharmaceutical compound recited in claim 5 wherein:

the dotted lines in formula 1 indicate a single or a double bond;

R₁ is selected from the group consisting of hydrogen, hydroxy, nitrate ester (ONO₂), halogen, thiol, heterocyclic group of 3 to 4 carbon atoms and 1 to 2 hetero atoms, nitroxyalkanoyl group of 2 to about 4 carbon atoms, lower alkoxy group of 1 to about 4 carbon atoms, lower alkyl group of 1 to about 4 carbon atoms, wherein all said radicals may optionally be substituted with hydroxy, chloro, fluoro, lower alkyl, lower alkenyl, lower alkynyl, lower alkoxy, amino, nitro, nitril, carboxyl and haloalkyl radicals; or R₁ is a group of formula OCO—R₇ wherein R₇ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms or lower alkoxy group of 1 to about 4 carbon atoms group;

R₂ is nitrate ester(ONO₂);

R₃ and R₄ are independently selected from the group consisting of hydrogen, hydroxy, nitrate ester (ONO₂), nitroxyalkanoyl group of 2 to about 4 carbon atoms, lower alkyl group of 1 to about 4 carbon atoms, lower alkenyl group of 2 to about 4 carbon atoms, lower alkynyl group of 2 to about 4 carbon atoms, lower alkoxy group of 1 to about 4 carbon atoms, wherein all said radicals may optionally be substituted with hydroxy, lower alkyl, lower alkenyl, lower alkynyl, lower alkoxy, amino, nitro and haloalkyl radicals, or R₃ and R₄ is a group of the formula OCO—R₈ wherein R₈ is 2-furanyl, lower alkyl group of 1 to about 4 carbon atoms or lower alkoxy group of 1 to about 4 carbon atoms; or R₃ and R₄ may together optionally form a cylic structure of the formula:

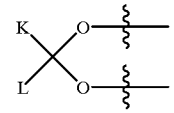

wherein, K and L are selected from the group consisting of hydrogen, and lower alkyl group of 1 to about 6 carbon atoms; optionally K and L can form a alicyclic ring of 5–8 carbon atoms or a heterocyclic ring of 4–5 carbon atoms and 1–2 heteroatoms selected from nitrogen, oxygen or sulfur;

R₅ is hydrogen or halogen;

R₆ is hydrogen, hydroxy, or oxygen;

P and Q are independently selected from the group consisting of hydrogen; chloro, fluoro and lower alkyl group of 1 to 4 carbon atoms; and X is methylene or sulfur if R₁ is a haloalkyl; and together with a pharmaceutically acceptable carrier.

8. A method of treating a patient with smooth muscle contractions by administering a therapeutically effective amount of the pharmaceutical compound recited in claim 5 wherein:

the dotted lines in formula 1 indicate a single or a double bond;

R₁ is selected from the group consisting of hydrogen, hydroxy, nitrate ester (ONO₂), chloro, thiol, lower alkyl group of 1 to 4 carbon atoms; or R₁ is a group of the formula OCO—R₇ wherein R₇ is propanoic acid, methyl or ethyl;

R₂ is nitrate ester (ONO₂);

R₃ and R₄ are independently selected from the group consisting of hydrogen, hydroxy, nitrate ester (ONO₂), methyl, lower alkynyl group of 2 to 4 carbon atoms; or $R_3$ and $R_4$ are of formula $OCO-R_8$ wherein $R_8$ is ethoxy, 2-furanyl, methyl, ethyl, propyl or butyl; or $R_3$ and $R_4$ may together optionally form a cylic structure of the formula:

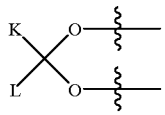

wherein, K and L are selected from the group consisting of hydrogen, methyl and butyl; or K and L can optionally form a cyclopentyl or cyclohexyl ring;

$R_5$ is hydrogen, chloro or bromo;

$R_6$ is hydroxy or oxygen;

P and Q are independently selected from a group of hydrogen, chloro, fluoro and methyl; and X is methylene; and together with a pharmaceutically acceptable carrier.

9. A method of treating a patient with undesired smooth muscle contractions and inflammation by administering a therapeutically effective amount of the pharmaceutical composition having the formula:

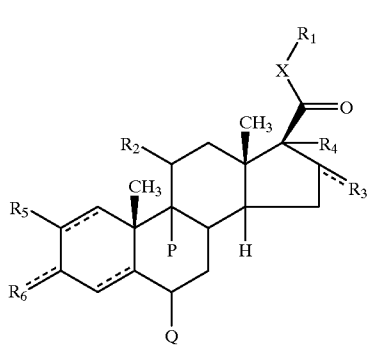

1 and pharmaceutically acceptable ester and prodrugs thereof, wherein;

the dotted lines in formula 1 indicate a single or a double bond;

$R_1$ is selected from the group consisting of hydrogen, hydroxy, nitrate ester ($ONO_2$), halogen, haloalkyl, nitroxyalkanoyl, thiol, heterocyclic, lower alkoxy, alkylsilyloxy, lower alkyl, wherein all said radicals may optionally be substituted with hydroxy, halogen, lower alkyl, lower alkenyl, lower alkynyl, lower alkoxy, amino, nitro, nitril, carboxyl and haloalkyl radicals or $R_1$ is a group of the formula $OCO-R_7$ wherein $R_7$ is alkanoic acid, lower alkyl, lower alkenyl, lower alkynyl, or lower alkoxy;

$R_2$ is nitrate ester ($ONO_2$);

$R_3$ and $R_4$ are independently selected from the group consisting of hydrogen, hydroxy, nitrate ester ($ONO_2$), nitroxyalkanoyl, lower alkyl, lower alkenyl, lower alkynyl and lower alkoxy, wherein all said radicals may optionally be substituted with hydroxy, lower alkyl, lower alkenyl, lower alkynyl, lower alkoxy, amino, nitro, nitril, carboxyl and haloalkyl radicals, or $R_3$ and $R_4$ are independently selected from a group of the formula $OCO-R_8$ wherein $R_8$ is 2-furanyl, lower alkyl or lower alkoxy group, or $R_3$ and $R_4$ may optionally form a cylic structure of the formula:

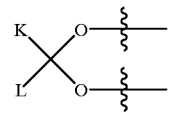

wherein, K and L are selected from the group consisting of hydrogen, and lower alkyl or optionally K and L can form a alicyclic ring or heterocyclic ring;

$R_5$ is hydrogen or halogen;

$R_6$ is hydrogen, hydroxy, or oxygen;

P and Q are independently selected from the group of hydrogen, chloro, fluoro and lower alkyl; and X is lower alkyl or sulfur if $R_1$ is haloalkyl; and together with a pharmaceutically acceptable carrier.

10. A method of treating a patient with undesired smooth muscle contractions and inflammation by administering a therapeutically effective amount of the pharmaceutical compound recited in claim 9 wherein:

the dotted lines in formula 1 indicate a single or a double bond;

$R_1$ is selected from the group consisting of hydrogen, hydroxy, nitrate ester ($ONO_2$), halogen, heterocyclic group of 2 to 5 carbon atoms and 1 to 2 hetero atoms, nitroxyalkanoyl group of 2 to about 6 carbon atoms, thiol, haloalkyl group of 1 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, halogen, lower alkyl, lower alkenyl, lower alkynyl, lower alkoxy, amino, nitro, nitril, carboxyl and haloalkyl radicals, or $R_1$ is a group of the formula $OCO-R_7$ wherein $R_7$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms group;

$R_2$ is nitrate ester ($ONO_2$);

$R_3$ and $R_4$ are independently selected from the group consisting of hydrogen, hydroxy, nitrate ester ($ONO_2$), nitroxyalkanoyl group of 2 to about 6 carbon atoms, lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals or $R_3$ and $R_4$ are independently selected from a group of the formula $OCO-R_8$ wherein $R_8$ is 2-furanyl, lower alkyl group of 1 to about 6 carbon atoms or lower alkoxy group of 1 to about 6 carbon atoms;

$R_3$ and $R_4$ may optionally form a cylic structure of the formula;

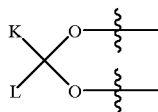

wherein, K and L are selected from the group consisting of hydrogen, lower alkyl group of 1 to about 8 carbon atoms, optionally K and L can form an alicyclic ring of 4 to about 8 carbon atoms or a heterocyclic ring of 4–6 carbon atoms and 1–2 heteroatoms selected from nitrogen, oxygen or sulfur;

$R_5$ is hydrogen or halogen;

$R_6$ is hydrogen, hydroxy or oxygen;

P and Q are independently selected from a group of hydrogen, chloro, fluoro and lower alkyl group of 1 to 6 carbon atoms; and X is lower alkyl group or sulfur if $R_1$ is a haloalkyl; and together with a pharmaceutically acceptable carrier.

11. A method of treating a patient with undesired smooth muscle contractions and inflammation by administering a therapeutically effective amount of the pharmaceutical compound recited in claim 9 wherein:

the dotted lines in formula 1 indicate a single or a double bond;

$R_1$ is selected from the group consisting of hydrogen, hydroxy, nitrate ester ($ONO_2$), halogen, thiol, heterocyclic group of 3 to 4 carbon atoms and 1 to 2 hetero atoms, nitroxyalkanoyl group of 2 to about 4 carbon atoms, lower alkoxy group of 1 to about 4 carbon atoms, lower alkyl group of 1 to about 4 carbon atoms, wherein all said radicals may optionally be substituted with hydroxy, chloro, fluoro, lower alkyl, lower alkenyl, lower alkynyl, lower alkoxy, amino, nitro, nitril, carboxyl and haloalkyl radicals; or $R_1$ is a group of formula OCO—$R_7$ wherein $R_7$ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms or lower alkoxy group of 1 to about 4 carbon atoms group;

$R_2$ is nitrate ester($ONO_2$);

$R_3$ and $R_4$ are independently selected from the group consisting of hydrogen, hydroxy, nitrate ester ($ONO_2$), nitroxyalkanoyl group of 2 to about 4 carbon atoms, lower alkyl group of 1 to about 4 carbon atoms, lower alkenyl group of 2 to about 4 carbon atoms, lower alkynyl group of 2 to about 4 carbon atoms, lower alkoxy group of 1 to about 4 carbon atoms, wherein all said radicals may optionally be substituted with hydroxy, lower alkyl, lower alkenyl, lower alkynyl, lower alkoxy, amino, nitro and haloalkyl radicals, or $R_3$ and $R_4$ is a group of the formula OCO—$R_8$ wherein $R_8$ is 2-furanyl, lower alkyl group of 1 to about 4 carbon atoms or lower alkoxy group of 1 to about 4 carbon atoms; or $R_3$ and $R_4$ may together optionally form a cylic structure of the formula:

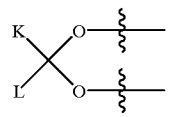

wherein, K and L are selected from the group consisting of hydrogen, and lower alkyl group of 1 to about 6 carbon atoms; optionally K and L can form a alicyclic ring of 5–8 carbon atoms or a heterocyclic ring of 4–5 carbon atoms and 1–2 heteroatoms selected from nitrogen, oxygen or sulfur;

$R_5$ is hydrogen or halogen;

$R_6$ is hydrogen, hydroxy, or oxygen;

P and Q are independently selected from the group consisting of hydrogen, chloro, fluoro and lower alkyl group of 1 to 4 carbon atoms; and X is methylene or sulfur if $R_1$ is a haloalkyl; and together with a pharmaceutically acceptable carrier.

12. A method of treating a patient with undesired smooth muscle contractions and inflammation by administering a therapeutically effective amount of the pharmaceutical compound recited in claim 9 wherein:

the dotted lines in formula 1 indicate a single or a double bond;

$R_1$ is selected from the group consisting of hydrogen, hydroxy, nitrate ester ($ONO_2$), chloro, thiol, lower alkyl group of 1 to 4 carbon atoms; or $R_1$ is a group of the formula OCO—$R_7$ wherein $R_7$ is propanoic acid, methyl or ethyl;

$R_2$ is nitrate ester ($ONO_2$);

$R_3$ and $R_4$ are independently selected from the group consisting of hydrogen, hydroxy, nitrate ester ($ONO_2$), methyl, lower alkynyl group of 2 to 4 carbon atoms; or $R_3$ and $R_4$ are of formula OCO—$R_8$ wherein $R_8$ is ethoxy, 2-furanyl, methyl, ethyl, propyl or butyl; or $R_3$ and $R_4$ may together optionally form a cylic structure of the formula:

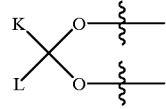

wherein, K and L are selected from the group consisting of hydrogen, methyl and butyl; or K and L can optionally form a cyclopentyl or cyclohexyl ring;

$R_5$ is hydrogen, chloro or bromo;

$R_6$ is hydroxy or oxygen;

P and Q are independently selected from a group of hydrogen, chloro, fluoro and methyl; and X is methylene; and together with a pharmaceutically acceptable carrier.

* * * * *